United States Patent [19]

Childress et al.

[11] Patent Number: 4,761,492

[45] Date of Patent: Aug. 2, 1988

[54] PROCESS FOR RECOVERING TRIMETHOXYSILANE FROM A TRIMETHOXYSILANE AND METHANOL MIXTURE

[75] Inventors: Thomas E. Childress, Newport; George M. Omietanski; Frank D. Mendicino, both of Marietta, all of Ohio

[73] Assignee: Union Carbide Corporation, Danbury, Conn.

[21] Appl. No.: 101,408

[22] Filed: Sep. 28, 1987

[51] Int. Cl.$^4$ ................................................. C07F 7/04
[52] U.S. Cl. ...................................... 556/482; 556/466; 203/51; 203/66; 203/81
[58] Field of Search ................. 556/466, 482; 203/51, 203/66, 81

[56] References Cited

U.S. PATENT DOCUMENTS

| 2,473,260 | 6/1949 | Rochow | 260/448.8 |
|---|---|---|---|
| 3,072,700 | 1/1963 | de Wit | 260/448.8 |
| 3,627,807 | 12/1971 | Bleh et al. | 260/448.8 A |
| 3,641,077 | 2/1972 | Rochow | 260/429 R |
| 3,775,457 | 11/1973 | Marsoka et al. | 260/448.8 R |
| 3,803,197 | 4/1974 | Anderson et al. | 260/448.8 A |
| 4,113,761 | 9/1978 | Kreuzburg et al. | 260/448.8 A |
| 4,185,029 | 1/1980 | Kreuzburg et al. | 260/448.8 A |
| 4,288,604 | 9/1981 | Magee et al. | 556/470 |
| 4,289,889 | 9/1981 | Herdle et al. | 556/470 |
| 4,323,690 | 4/1982 | Montle et al. | 556/470 |
| 4,402,797 | 9/1983 | Halm et al. | 556/466 X |
| 4,447,632 | 5/1984 | Mallon | 556/470 |
| 4,487,949 | 12/1984 | Mallon | 556/470 |
| 4,697,027 | 9/1987 | Sugihara et al. | 556/482 X |
| 4,911,740 | 10/1983 | Flaningam et al. | 556/466 X |

FOREIGN PATENT DOCUMENTS

| 163529 | 8/1979 | Japan | 556/470 UX |
|---|---|---|---|
| 84348 | 1/1980 | Japan | 556/470 UX |
| 33457 | 3/1980 | Japan | 556/470 UX |
| 72198 | 5/1980 | Japan | 556/470 UX |
| 72197 | 5/1980 | Japan | 556/470 UX |
| 2641 | 5/1980 | Japan | 556/470 UX |
| 28928 | 7/1980 | Japan | 556/470 UX |
| 28929 | 7/1980 | Japan | 556/470 UX |
| 16492 | 4/1981 | Japan | 556/470 UX |

*Primary Examiner*—Paul F. Shaver
*Attorney, Agent, or Firm*—Steven H. Flynn

[57] ABSTRACT

An extractive distillation process for recovering trimethoxysilane from a trimethoxysilane-methanol mixture is provided using as the extractive solvent tetramethoxysilane.

9 Claims, 1 Drawing Sheet

PROCESS FOR RECOVERING TRIMETHOXYSILANE FROM A TRIMETHOXYSILANE AND METHANOL MIXTURE

BACKGROUND OF THE INVENTION (a) Field of the Invention

The present invention relates to a process for recovering trimethoxysilane and in particular to a process for recovering trimethoxysilane from a mixture of trimethoxysilane and methanol.

The present invention also relates to a continuous process for producing and purifying trimethoxysilane by first reacting silicon metal and methanol in the presence of a copper catalyst to produce a product which includes, along with trimethoxysilane, a trimethoxysilane-methanolazeotrope. Thereafter using tetramethoxysilane an extractive distillation is performed to recover trimethoxysilane from the mixture. The methanol separated from the tetramethoxysilane/trimethoxysilane mixture can be recycled for use in the reaction while the tetramethoxysilane can be reused as the extractive distillation solvent.

(b) Prior Art

The reaction between silicon metal and alcohol is well established. As long ago as 1949, U.S. Pat. No. 2,473,260 issued to Rochow described a process for the preparation of methyl silicates from methanol and silicon-copper masses. Similarly, U.S. Pat. No. 3,072,700 taught the preparation of silanes [(RO)$_3$SiH, (RO)$_2$SiH$_2$] from silicon metal and alcohol in a fluidized bed reactor.

Patents on the similar production of tetraalkylorthosilicates include U.S. Pat. No. 4,288,604 and Japanese Pat. No. 1979-163529. Patents covering the similar production of trialkoxysilanes include U.S. Pat. No. 3,775,457. See also Japanese Pat. Nos. 1979-163529, 1980-28929, 1980-28928, 1980-2641, and Japanese laid-open application Nos. 33457/1980 and 11538/1980.

However any synthesis of trimethoxysilane which employs an excess amount of methanol is plagued by the loss of trimethoxysilane in an azeotrope with the excess methanol since trimethoxysilane and methanol form a minimum boiling azeotrope. Only that component of the trimethoxysilane and methanol mixture which is present in excess of the azeotropic proportion can be recovered by simple distillation techniques.

In Japanese Pat. Nos. 11538/1980 and 33457/1980 there is disclosed a process employing azeotropic distillations which have employed hexane in an attempt to form a second azeotrope with methanol which can then be boiled off to leave trimethoxysilane behind as an end product. This technique is not preferred since it introduces a new component to the system which may contaminate the end product and increases the cost of the final product. Also, this technique is difficult to control in a continuous mode, since it requires maintaining by continuous feed the exact ratio of hexane and methanol to form the lower boiling azeotrope between methanol and hexane. Finally, hexane and trimethoxysilane can form an azeotrope which will complicate the recovery of trimethoxysilane.

Accordingly, a need continues to exist for a commercially attractive process to recover trimethoxysilane from a trimethoxysilane-methanolazeotrope.

OBJECTIVES OF THE INVENTION

It is a primary object of the present invention to produce an economical and efficient method for recovering trimethoxysilane from a trimethoxysilane-methanol mixture, and in particular from an azeotrope formed during the copper catalyzed reaction between silicon metal and methanol.

Another object of the present invention is to provide such a process as is capable of being integrated into a continuous process for the manufacture of trimethoxysilane.

Other objects and advantages of the present invention will be made apparent by the description and examples which follow.

SUMMARY OF THE INVENTION

The present invention provides a process for recovering trimethoxysilane from a mixture of trimethoxysilane and methanol that is capable of forming an azeotrope comprising:

(a) feeding a mixture of trimethoxysilane and methanol to a first distillation zone;

(b) adding sufficient solvent to the first distillation zone to increase the volatility of the methanol relative to the volatility of the trimethoxysilane-solvent mixture;

(c) increasing the temperature in the first distillation zone to distill the methanol from the solvent/trimethoxysilane mixture;

(d) removing the solvent/trimethoxysilane mixture to a second distillation zone; and (e) increasing the temperature in the second distillation zone to distill the trimethoxysilane from the solvent.

In general, the solvent is a high boiling material which has greater affinity for trimethoxysilane than for methanol. In the present invention, the trimethoxysilane is preferentially extracted down the distillation zone while methanol is taken overhead. Solvent and trimethoxysilane are separated in a second distillation zone. The solvent must be unreactive and non-azeotropic with both methanol and trimethoxysilane, preferably the solvent is tetramethoxysilane.

DETAILED DESCRIPTION OF THE DRAWING

Figure 1:
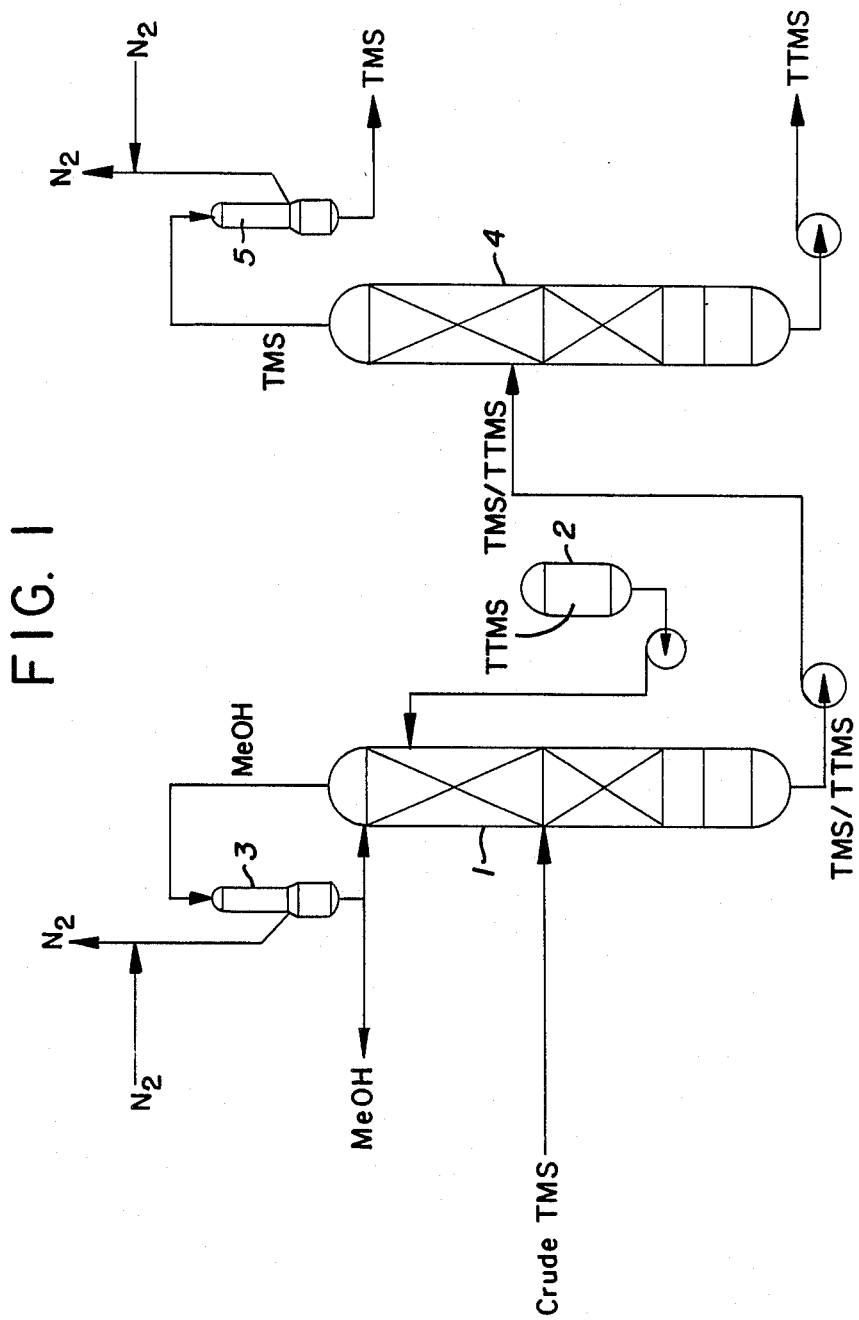
FIG. 1 illustrates schematically the material flow and operational steps used in practicing the present invention.

FIG. 1 illustrates a process for recovering trimethoxysilane (TMS) from crude TMS using tetramethoxysilane (TTMS) in an extractive distillation. Crude TMS (preferably from the reaction system) containing a TMS-methanol azeotrope is fed into a first distillation zone (1). TTMS from a storage tank (2) is fed near the top of the first distillation zone (1). The first distillation is run under an inert atmosphere to exclude moisture, preferably a nitrogen blanket. Methanol is taken off overhead and passed through a condensor (3) to condense the methanol. A portion of the condensed methanol is returned to the top of the first distillation zone as a reflux, the remaining condensed methanol is ready to be recycled to a silicon metal-methanol reaction. Coming out the bottom of the first distillation zone (1) is TMS and TTMS. The mixture of TMS and TTMS is fed into a second distillation zone (4). The second distillation is run under an inert atmosphere to exclude moisture, preferably a nitrogen blanket. TMS is taken off overhead and passed through a condenser (5) to condense the TMS. Coming out the bottom of the second distillation zone (4) is TTMS, which can be recycled to the TTMS storage tank (2) for reuse in the first distillation zone (1).

DETAILED DESCRIPTION OF THE INVENTION

In accordance with the present invention there is provided a process for recovering trimethoxysilane from an azeotropic mixture of trimethoxysilane and methanol. In the synthesis of trimethoxysilane which employs more than the stoichiometric amount of methanol a loss of trimethoxysilane can result from the azeotrope formed between trimethoxysilane and methanol. For instance, in the production of trimethoxysilane from silicon metal and methanol in the presence of a copper catalyst the reaction products generally consist of trimethoxysilane, hydrogen, unreacted methanol and an azeotrope of trimethoxysilane and methanol.

$$Si + 3MeOH \xrightarrow{catalyst} HSi(OMe)_3 + H_2$$

The bulk of the chemical reactions are run in the liquid phase on the surface of the silicon metal. For this reason, the reaction is generally run in a slurry reactor by charging silicon metal and catalyst to the reactor with an appropriate liquid to form a slurry. Zarochak, M. F., Pennline, H. W., and Schehl, R. R., "An Experimental Reactor System for Investigation of Indirect Liquefaction Catalysts in Slurry Phase Operation", Technical Information Center—Office of Scientific and Technical Information—U.S. Department of Energy, DE84007876, February 1984. This material is then heated to reaction temperatures ranging from 150° C. to 260° C., preferably 200°–240° C. at which point methanol is fed at a controlled, continuous rate. After a short initiation period, trimethoxysilane formation starts. The unreacted methanol, hydrogen by-product, and crude trimethoxysilane are continuously removed from the slurry reactor.

The second step is the trimethoxysilane recovery which should be coupled to the reactor to minimize side reactions. Crude trimethoxysilane is initially condensed to remove by-product hydrogen and then fed to the recovery system. The recovery system consists of two distillation zones. The first zone is used to break the methanol/trimethoxysilane azeotrope by running an extractive distillation using tetramethoxysilane.

Tetramethoxysilane is added to the first distillation zone to raise the volatility of the methanol relative to the volatility of the trimethoxysilane. Preferably the amount of tetramethoxysilane added to the first distillation zone is sufficient to raise the relative volatility of the methanol as compared to the trimethoxysilane to a value greater than one for all proportions of the methanol/trimethoxysilane azeotrope.

The process is preferably run in a continuous mode which, in turn, requires the use of a larger amount of tetramethoxysilane to assure that the relative volatility of the methanol is higher for crude compositions having varying amounts of trimethoxysilane.

The amount, by weight, of tetramethoxysilane fed to the first distillation zone in comparison to the amount of crude product fed to the first distillation zone is from 1:1 to 10:1, there being no advantage to higher levels of tetramethoxysilane, preferably 3:1 to 6:1.

The tetramethoxysilane is fed near the top of the first zone to extract the trimethoxysilane out of the methanol/trimethoxysilane azeotropic mixture. Coming out the bottom of the first zone will be trimethoxysilane and extractant tetramethoxysilane. The overhead from the first zone will be methanol which should be recycled directly back into the reactor.

The second distillation zone is used to separate trimethoxysilane from tetramethoxysilane. Trimethoxysilane is taken off overhead while the tetramethoxysilane is taken off near or at the bottom of the second zone. The heavies are also removed from the system off the bottom of the second zone.

The process of the present invention can be performed in any conventional distillation apparatus, and can be run as a batch, semi-batch or continuous process. Preferably the distillation is run as a continuous process in an extractive distillation column such as a tray tower or a packed tower.

The temperature of the materials fed to the distillation zones is not critical and can vary widely. Usually the materials are fed as liquids near their boiling points to minimize heat loss within each distillation column and promote energy efficiency.

The pressure within the distillation zones is likewise not critical, with atmospheric pressure being most preferred.

The trimethoxysilane and tetramethoxysilane mixture is easily separated in the second distillation zone by conventional means. Usually the trimethoxysilane can be removed from the mixture by simple distillation. The tetramethoxysilane is then preferably recycled for use as the extractive distillation solvent in subsequent separations of trimethoxysilane/methanol azeotropes.

It may be useful to add inhibitors to the first distillation zone in an effort to provide increased stability to the crude trimethoxysilane. Such inhibitors, when employed, should be added to the top of the first distillation zone in an amount ranging from 0.1 to 1.0 weight percent, based on the weight of the trimethoxysilane crude. Preferably, these inhibitors will be metal complexing agents such as pentanedione or triphenylphosphine.

Whereas the exact scope of the instant invention is set forth in the appended claims, the following specific examples illustrate certain aspects of the present invention and, more particularly, point out methods of evaluating the same. However, the examples are set forth for illustration only and are not to be construed as limitations on the present invention except as set forth in the appended claims. All parts and percentages are by weight unless otherwise specified.

EXAMPLES

The following examples were run in a 12 foot glass Oldershaw distillation unit consisting of an one-inch, 50 tray distillation column fitted into the neck of a 1 liter reboiler and fitted with a reflux condenser equipped with an automatic reflux splitter controlled by a timer.

Heat supplied to the reboiler was controlled by monitoring the temperature in the fifth tray (trays are numbered sequentially from the bottom to the top). Crude trimethoxysilane was fed to the 15th tray. Tetramethoxysilane was fed to the 40th tray. The temperature of the reboiler, 5th tray, 15th tray, 40th tray, 45th tray and condenser were measured using a thermocouple.

Crude trimethoxysilane and tetramethoxysilane were continuously fed to the column. Methanol was continuously removed overhead. Trimethoxysilane/tetramethoxysilane mixture was removed as a bottom product. Samples were analyzed by gas chromatography.

The trimethoxysilane crude was generated from the MeOH-Si reaction carried out in the CHEMINEER ™ Reactor. Normally, technical grade MeOH was added to increase MeOH content to at least 50 wt. %.

Tetramethoxysilane was produced from trimethoxysilane and methanol using a tertiary amine as the catalyst. The reaction product was batch distilled using a 20-tray Oldershaw column to yield ≧99.5% tetramethoxysilane.

Preliminary runs showed that the trimethoxysilane crude was unstable due to the following side reaction: (TMS-trimethoxysilane, TTMS-tetramethoxysilane).

$$MeOH + TMS \rightarrow TTMS + H_2$$

Therefore inhibitor was added to the trimethoxysilane and tetramethoxysilane feed tanks and to the overhead and bottoms samples.

| Location | Inhibitor |
|---|---|
| TMS Crude Feed Tank | 0.1 wt % 2,4-Pentanedione (AcAc) |
|  | 1 wt % Triphenylphosphine (TPP) |
| TTMS Feed Tank | 0.1 wt % AcAc |
|  | 0.1 wt % TPP |
| Overhead Sample | 0.2 wt % AcAc |
|  | 1 wt % TPP |
| Bottom Sample | 0.2 wt % AcAc |
|  | 1 wt % TPP |

By adding inhibitor to both feeds, the side reaction was suppressed in the crude feed tank and most of the distillation column. AcAc and TPP boil significantly higher than trimethoxysilane. Therefore, trays above the tetramethoxysilane feed point, Tray #41–50 from bottom, would not be inhibited.

Once the system was up and running, the overhead and bottoms were sampled every half hour. Most conditions were run for 1.5 hours in order that steady state could be obtained. Since runs were limited to about 5 hours due to feed tanks and receiver volumes, only 3 test conditions could be studied per run.

In general, when TMS/MeOH crude is fed to a simple distillation system, separate high purity MeOH and high purity TMS streams are not obtained. In example 1–18 the MeOH/TMS feed ratio was greater than the azeotropic ratio of 45/55. The best separation that simple distillation could produce would be an overhead containing the azeotropic MeOH/TMS ratio and a TMS-free bottoms stream. In examples 19 and 20, the MeOH/TMS feed ratio was less than the azeotropic ratio and the best separation that simple distillation could produce would be an overhead containing the azeotropic ratio and a MeOH-free bottoms stream.

However, by using extractive distillation with TTMS as the solvent, separate high purity MeOH and high purity TMS streams were obtained. All data from runs carried out in the extractive distillation column are presented in Table 1 as examples 1–20. Table 2 presents this same data in terms of only MeOH and TMS, i.e. on a solvent and impurity-free basis. This data clearly shows that for each example, MeOH and TMS have been almost completely separated. As discussed above such results cannot be achieved via simple distillation.

In order to produce a high purity TMS product stream and a high purity TTMS stream for recycle, it is necessary to distill the bottoms stream from the extractive distillation column. This was done using simple distillation in a "solvent recovery column". The experimental apparatus consisted of a 50-tray, 28 mm diameter glass Oldershaw column. The feed consisted of bottoms which had been previously produced in the extractive distillation column.

The solvent recovery column was operated continuously: Crude TMS/TTMS was continuously fed to Tray 40 while overhead and bottoms were continuously removed. Tray 45 temperature was used to control heat imput to the reboiler. Reflux ratio was controlled using a timer. Feed, overhead, and bottoms samples were analyzed by Gas Chromatography. The results of these experiments, examples 21–23, are presented in Table 3. As demonstrated, high purity TMS and TTMS streams were obtained.

TABLE 1

| Example No. | TMS Crude Rate, g/hr. | S/F[1] | R[2] | Tray 5 Temp, °C. | Sample | MeOH | Lites | TMS | Me—TMS | TTMS | Disiloxane Heavies | Heavies |
|---|---|---|---|---|---|---|---|---|---|---|---|---|
| \multicolumn{13}{c}{EXTRACTIVE DISTILLATION} ||||||||||||
| Crude TMS composition for Examples 1–3 |  |  |  |  |  | 49.7 | 0.1 | 43.7 | — | 3.9 | 0.1 | 2.0 |
| 1 | 157 | 3 | 1.5 | 74 | Overhead | 93.7 | 0.1 | 2.0 | 0.039 | 4.0 | Trace | 0.2 |
|  |  |  |  |  | Bottoms | 0.026 | — | 12.2 | 0.165 | 86.2 | 0.6 | 0.8 |
| 2 | 147 | 3 | 2.5 | 75 | Overhead | 93.6 | 0.1 | 3.2 | 0.042 | 2.9 | Trace | 0.2 |
|  |  |  |  |  | Bottoms | 0.043 | — | 12.6 | 0.141 | 86.0 | 0.4 | 0.9 |
| 3 | 151 | 3 | 1.0 | 74 | Overhead | 92.9 | 0.1 | 1.8 | 0.04 | 5.0 | Trace | 0.2 |
|  |  |  |  |  | Bottoms | 0.049 | — | 12.0 | 0.151 | 86.5 | 0.4 | 0.9 |
| Crude TMS composition for Examples 4–6 |  |  |  |  |  | 49.8 | 0.1 | 41.3 | 0.058 | 5.9 | 1.0 | 1.8 |
| 4 | 158 | 3 | 1.0 | 74 | Overhead | 93.1 | 0.1 | 1.4 | 0.022 | 5.2 | Trace | 0.2 |
|  |  |  |  |  | Bottoms | 0.017 | — | 11.9 | 0.063 | 86.4 | 0.4 | 1.2 |
| 5 | 158 | 3 | 0.75 | 74 | Overhead | 91.3 | 0.1 | 1.0 | 0.024 | 7.4 | — | 0.2 |
|  |  |  |  |  | Bottoms | 0.026 | — | 12.5 | 0.039 | 85.9 | 0.3 | 1.3 |
| 6 | 151 | 3 | 0.5 | 75 | Overhead | 89.8 | 0.1 | 0.8 | 0.033 | 8.9 | — | 0.4 |
|  |  |  |  |  | Bottoms | 0.04 | — | 12.5 | 0.043 | 85.7 | 0.3 | 1.2 |
| Crude TMS composition for Examples 7–9 |  |  |  |  |  | 51.3 | 0.1 | 37.5 | 0.047 | 8.0 | 1.1 | 2.0 |
| 7 | 152 | 4 | 1.0 | 81 | Overhead | 93.4 | 0.1 | 0.23 | 0.046 | 6.0 | — | 0.2 |
|  |  |  |  |  | Bottoms | 0.024 | — | 8.5 | 0.087 | 89.2 | 0.4 | 1.8 |
| 8 | 151 | 4 | 0.75 | 79 | Overhead | 90.7 | 0.1 | 0.13 | 0.053 | 8.7 | — | 0.3 |
|  |  |  |  |  | Bottoms | 0.014 | — | 8.7 | 0.095 | 89.5 | 0.3 | 1.4 |
| 9 | 151 | 4 | 0.5 | 79 | Overhead | 89.0 | 0.1 | 0.11 | 0.058 | 10.3 | — | 0.4 |
|  |  |  |  |  | Bottoms | 0.014 | — | 8.7 | 0.091 | 89.7 | 0.3 | 1.2 |
| Crude TMS composition for Examples 10–12 |  |  |  |  |  | 49.5 | 0.1 | 37.8 | 0.055 | 8.5 | 0.5 | 3.2 |
| 10 | 156 | 2 | 1.0 | 74 | Overhead | 88.7 | 0.1 | 5.9 | 0.017 | 4.5 | — | 0.8 |

TABLE 1-continued

EXTRACTIVE DISTILLATION

| Example No. | TMS Crude Rate, g/hr. | S/F[1] | R[2] | Tray 5 Temp, °C. | Sample | MeOH | Lites | TMS | Me—TMS | TTMS | Disiloxane Heavies | Heavies |
|---|---|---|---|---|---|---|---|---|---|---|---|---|
|  |  |  |  |  | Bottoms | 0.014 | — | 10.2 | 0.098 | 87.4 | 0.4 | 1.9 |
| 11 | 158 | 2 | 1.5 | 73 | Overhead | 88.8 | 0.1 | 7.4 | 0.019 | 3.5 | — | 0.2 |
|  |  |  |  |  | Bottoms | 0.016 | — | 12.9 | 0.099 | 84.5 | 0.5 | 2.0 |
| 12 | 152 | 2 | 2.5 | 73 | Overhead | 85.7 | 0.1 | 12.2 | 0.019 | 1.8 | — | 0.2 |
|  |  |  |  |  | Bottoms | 0.003 | — | 14.1 | 0.09 | 83.0 | 0.4 | 2.5 |
| Crude TMS composition for Examples 13-15 |  |  |  |  |  | 48.1 | 0.1 | 43.7 | 0.033 | 5.2 | 1.0 | 1.6 |
| 13 | 157 | 3 | 1.25 | 76 | Overhead | 93.9 | 0.15 | 0.58 | 0.036 | 4.9 | 0.009 | 0.41 |
|  |  |  |  |  | Bottoms | 0.123 | — | 9.95 | 0.54 | 88.3 | 0.5 | 1.1 |
| 14 | 158 | 3 | 2.0 | 73 | Overhead | 95.2 | 0.17 | 0.86 | 0.02 | 3.54 | 0.04 | 0.21 |
|  |  |  |  |  | Bottoms | 0.100 | — | 11.95 | 0.04 | 86.4 | 0.5 | 1.0 |
| 15 | 155 | 3 | 3.5 | 70 | Overhead | 93.8 | 0.17 | 3.5 | 0.02 | 2.0 | 0.2 | 0.3 |
|  |  |  |  |  | Bottoms | 0.094 | — | 12.2 | 0.02 | 86.2 | 0.5 | 1.0 |
| Crude TMS composition for Examples 16-18 |  |  |  |  |  | 80.3 | 0.009 | 16.6 | — | 1.5 | 0.5 | 0.36 |
| 16 | 94 | 5 | 1.5 | 92 | Overhead | 94.7 | — | 0.16 | 0.07 | 4.8 | — | 0.3 |
|  |  |  |  |  | Bottoms | 0.041 | — | 1.53 | 0.07 | 97.4 | 0.25 | 0.7 |
| 17 | 93 | 5 | 2.0 | 102 | Overhead | 95.8 | — | 0.47 | 0.06 | 3.6 | — | 0.15 |
|  |  |  |  |  | Bottoms | 0.05 | — | 2.22 | 0.07 | 96.82 | 0.31 | 0.53 |
| 18 | 93 | 5 | 2.5 | 101 | Overhead | 95.6 | — | 1.02 | 0.065 | 3.1 | 0.02 | 0.21 |
|  |  |  |  |  | Bottoms | 0.03 | — | 2.5 | 0.061 | 96.5 | 0.3 | 0.53 |
|  |  |  |  |  | Feed for Examples 19-20 | 20.6 | 0.24 | 63.5 | 0.1 | 12.3 | 1.61 | 0.61 |
| 19 | 92 | 5 | 3 | 96 | Overhead | 92.8 | 0.83 | 0.92 | 0.28 | 4.7 | 0.05 | 0.34 |
|  |  |  |  |  | Bottoms | 0.123 | — | 13.1 | 0.07 | 85.4 | 0.14 | 0.86 |
| 20 | 90 | 5 | 4 | 87 | Overhead | 93.6 | 0.84 | 0.39 | 0.18 | 4.5 | 0.04 | 0.42 |
|  |  |  |  |  | Bottoms | 0.08 | — | 13.4 | 0.06 | 85.5 | 0.33 | 0.59 |

TTMS — tetramethoxysilane
TMS — trimethoxysilane
[1]S/F = solvent/feed = TTMS lb/hr/TMS lb/hr
[2]R = reflux ratio = reflux lb/hr/take-off lb/hr

TABLE 2

SEPARATION EFFICIENCY FOR EXAMPLE 1-20

| Example No. | Sample | MeOH*[1] | TMS*[1] | % MeOH Recovery[2] Overhead | % TMS Recovery[3] in Bottoms |
|---|---|---|---|---|---|
| 1 | Overhead | 97.9 | 2.1 | 99.8 | 97.6 |
|  | Bottoms | 0.2 |  |  |  |
| 2. | Overhead | 96.7 | 3.3 | 99.7 | 96.1 |
|  | Bottoms | 0.3 | 99.7 |  |  |
| 3. | Overhead | 98.1 | 1.9 | 99.7 | 97.8 |
|  | Bottoms | 0.4 | 99.6 |  |  |
| 4. | Overhead | 98.5 | 1.5 | 99.9 | 98.2 |
|  | Bottoms | 0.1 | 99.9 |  |  |
| 5. | Overhead | 98.9 | 1.1 | 99.8 | 98.7 |
|  | Bottoms | 0.2 | 99.8 |  |  |
| 6. | Overhead | 99.1 | 0.9 | 99.8 | 98.9 |
|  | Bottoms | 0.3 | 99.7 |  |  |
| 7. | Overhead | 99.8 | 0.2 | 99.8 | 99.7 |
|  | Bottoms | 0.3 | 99.7 |  |  |
| 8. | Overhead | 99.9 | 0.1 | 99.9 | 99.9 |
|  | Bottoms | 0.2 | 99.8 |  |  |
| 9. | Overhead | 99.9 | 0.1 | 99.9 | 99.9 |
|  | Bottoms | 0.2 | 99.8 |  |  |
| 10. | Overhead | 93.8 | 6.2 | 99.9 | 91.4 |
|  | Bottoms | 0.1 | 99.9 |  |  |
| 11. | Overhead | 92.3 | 7.7 | 99.9 | 89.1 |
|  | Bottoms | 0.1 | 99.9 |  |  |
| 12. | Overhead | 87.5 | 12.5 | 99.9 | 81.3 |
|  | Bottoms | 0.02 | 99.98 |  |  |
| 13. | Overhead | 99.4 | 0.6 | 98.9 | 99.3 |
|  | Bottoms | 1.2 | 98.8 |  |  |
| 14. | Overhead | 99.1 | 0.9 | 98.9 | 99.3 |
|  | Bottoms | 0.8 | 99.2 |  |  |
| 15. | Overhead | 96.4 | 3.6 | 99.3 | 95.9 |
|  | Bottoms | 0.8 | 99.2 |  |  |
| 16. | Overhead | 99.8 | 0.2 | 99.5 | 99.0 |
|  | Bottoms | 2.6 | 97.4 |  |  |
| 17. | Overhead | 99.5 | 0.5 | 99.5 | 97.6 |
|  | Bottoms | 2.2 | 97.8 |  |  |
| 18. | Overhead | 98.4 | 1.1 | 99.8 | 94.6 |
|  | Bottoms | 1.2 | 98.8 |  |  |
| 19. | Overhead | 99.0 | 1.0 | 97.2 | 99.7 |
|  | Bottoms | 0.9 | 99.1 |  |  |
| 20. | Overhead | 99.6 | 0.4 | 98.1 | 99.9 |
|  | Bottoms | 0.6 | 99.4 |  |  |

[1]*Means on a solvent + Impurity free basis
[2]% MeOH Recovery = $\frac{\text{lb MeOH Overhead}}{\text{lb MeOH Fed}}$
[3]% TMS Recovery = $\frac{\text{lb TMS in Bottoms}}{\text{lb TMS Fed}}$

TABLE 3

TRIMETHOXYSILANE FROM SECOND DISTILLATION COLUMN
SIMULATION: Feed = 640 g/hr

| Example No. | R | Tray °C. | Sample | MeOH | Lites | TMS | Me—TMS | TTMS | Di-Siloxanes | Heavies |
|---|---|---|---|---|---|---|---|---|---|---|
|  |  |  | Feed for Examples 21-23 | 0.096 | — | 9.53 | — | 89.81 | 0.38 | 0.14 |
| 21 | 6/1 | 97 | Overhead | 0.44 | — | 98.27 | 0.032 | 0.52 | 0.04 | 0.377 |
|  |  |  | Bottoms | 0.019 | — | 0.005 | — | 98.67 | 0.05 | 0.57 |
| 22 |  | 99 | Overhead |  | — | 98.29 | 0.055 | 0.69 | 0.03 | 0.34 |
|  |  |  | Bottoms | 0.016 | — | — | — | 98.67 | 0.6 | 0.58 |
| 23 |  | 103 | Overhead | 0.23 | — | 97.56 | 0.11 | 1.63 | 0.04 | 0.4 |

TABLE 3-continued

TRIMETHOXYSILANE FROM SECOND DISTILLATION COLUMN
SIMULATION: Feed = 640 g/hr

| Example No. | R | Tray °C. | Sample | MeOH | Lites | TMS | Me—TMS | TTMS | Di-Siloxanes | Heavies |
|---|---|---|---|---|---|---|---|---|---|---|
| | | | Bottoms | 0.027 | — | — | — | 98.78 | 0.57 | 0.52 |

We claim:

1. A process for recovering trimethoxysilane from a mixture of trimethoxysilane and methanol which mixture is capable of forming an azeotrope comprising.
   (a) feeding a mixture of trimethoxysilane and methanol to a first distillation zone;
   (b) adding sufficient solvent to the first distillation zone to increase the volatility of the methanol relative to the volatility of the trimethoxysilane-solvent mixture;
   (c) increasing the temperature in the first distillation zone to distill the methanol from the solvent/trimethoxysilane mixture;
   (d) removing the solvent/trimethoxysilane mixture to a second distillation zone; and
   (e) increasing the temperature in the second distillation zone to distill the trimethoxysilane from the solvent.

2. The process of claim 1 wherein the solvent is a high boiling material which has a greater affinity for trimethoxysilane than for methanol.

3. The process of claim 2 wherein the solvent is tetramethoxysilane.

4. The process of claim 2 wherein the solvent is a disiloxane.

5. The process of claim 1 wherein the pressure of the first and second distillation zone is approximately atmospheric.

6. The process of claim 1 wherein from 0.1 to 1 weight percent, based on the weight of the mixture of trimethoxysilane and methanol fed into the first distillation zone, of an inhibitor is added to the first distillation zone.

7. The process of claim 6 wherein the inhibitor is a metal complexing agent.

8. The process of claim 7 wherein the inhibitor is either pentanedione or triphenylphosphine.

9. The process of claim 1 wherein the distillation in the first and second distillation zones is run as a continuous process.

* * * * *